(12) United States Patent
Ger et al.

(10) Patent No.: US 10,324,021 B2
(45) Date of Patent: Jun. 18, 2019

(54) MAGNETOPHORISIS MEASURING SYSTEM FOR DETERMINING MOTION STATUS OF OBJECT AND QUANTIFYING AMOUNT OF MAGNETIC PARTICLES CONTAINED THEREIN

(71) Applicant: Chung Yuan Christian University, Taoyuan (TW)

(72) Inventors: Tzong-Rong Ger, Taoyuan (TW); Wei-Yu Chen, New Taipei (TW); Ting-Ruei Wang, Taipei (TW); Hsiao-Hsuan Huang, New Taipei (TW); Wen-Wei Sun, Pingtung County (TW); Wan-Ying Huang, New Taipei (TW)

(73) Assignee: CHUNG YUAN CHRISTIAN UNIVERSITY, Taoyuan (TW)

( * ) Notice: Subject to any disclaimer, the term of this patent is extended or adjusted under 35 U.S.C. 154(b) by 98 days.

(21) Appl. No.: 15/587,081

(22) Filed: May 4, 2017

(65) Prior Publication Data
US 2018/0136111 A1    May 17, 2018

(30) Foreign Application Priority Data
Nov. 16, 2016    (TW) ............................. 105137453 A

(51) Int. Cl.
*G06T 7/13*    (2017.01)
*G01N 15/14*    (2006.01)
(Continued)

(52) U.S. Cl.
CPC ..... *G01N 15/1463* (2013.01); *G02B 21/0004* (2013.01); *G02B 21/02* (2013.01);
(Continued)

(58) Field of Classification Search
None
See application file for complete search history.

(56) References Cited

U.S. PATENT DOCUMENTS

| | | | |
|---|---|---|---|
| 5,974,901 A | 11/1999 | Zborowski et al. | |
| 2006/0252054 A1* | 11/2006 | Lin | A61M 1/36 435/6.11 |

(Continued)

FOREIGN PATENT DOCUMENTS

| | | |
|---|---|---|
| CN | 100388004 C | 5/2008 |
| JP | 2002-22704 A | 1/2002 |

(Continued)

OTHER PUBLICATIONS

Japan's 1st official action dated Oct. 24, 2016.
(Continued)

*Primary Examiner* — Vikkram Bali
(74) *Attorney, Agent, or Firm* — Chun-Ming Shih

(57) ABSTRACT

The present invention provides a magnetophorisis measuring system, comprising a microscope device, a magnetic field generator, an image capturing unit, and a processing unit. The microscope device is utilized to magnify a sample liquid having a plurality of objects respectively having a plurality of magnetic particles. The magnetic field generator is utilized to provide an external magnetic field on the sample liquid such that the objects are moved by the external magnetic field. The image capturing unit is utilized to capture a dynamic image with respect to the fluid sample in a view field of the microscope device. The processing unit receives the dynamic image, automatically detects and locks moving objects, determines a motion status corresponding to each object, and quantifies the magnetic particles according to motion status of each object.

16 Claims, 11 Drawing Sheets

(51) Int. Cl.

| | |
|---|---|
| *G06T 7/246* | (2017.01) |
| *G02B 21/02* | (2006.01) |
| *G02B 21/36* | (2006.01) |
| *H01F 6/06* | (2006.01) |
| *H04N 1/40* | (2006.01) |
| *H04N 7/18* | (2006.01) |
| *G02B 21/00* | (2006.01) |
| *G02B 21/24* | (2006.01) |
| *G06T 7/254* | (2017.01) |
| *G01N 15/10* | (2006.01) |
| *H01F 7/02* | (2006.01) |
| *H01F 7/20* | (2006.01) |

(52) U.S. Cl.
CPC ............ *G02B 21/24* (2013.01); *G02B 21/36* (2013.01); *G06T 7/13* (2017.01); *G06T 7/246* (2017.01); *G06T 7/254* (2017.01); *H01F 6/06* (2013.01); *H04N 1/40012* (2013.01); *H04N 7/183* (2013.01); *G01N 2015/1006* (2013.01); *G01N 2015/1075* (2013.01); *G06T 2207/10016* (2013.01); *G06T 2207/10056* (2013.01); *G06T 2207/30024* (2013.01); *G06T 2207/30072* (2013.01); *G06T 2207/30241* (2013.01); *H01F 7/0294* (2013.01); *H01F 7/20* (2013.01)

(56) References Cited

U.S. PATENT DOCUMENTS

| | | | |
|---|---|---|---|
| 2008/0023641 A1* | 1/2008 | Takeuchi | H01J 37/09 250/396 ML |
| 2008/0186551 A1* | 8/2008 | Hanft | A61F 9/0084 359/205.1 |
| 2011/0236882 A1 | 9/2011 | Lin et al. | |
| 2013/0054142 A1* | 2/2013 | Moriguchi | G06Q 10/06 701/519 |

FOREIGN PATENT DOCUMENTS

| | | |
|---|---|---|
| JP | 2009-536348 A | 10/2009 |
| JP | 2016/063912 A1 | 8/2017 |
| WO | WO2012060163 A1 | 5/2012 |

OTHER PUBLICATIONS

"Quantitative intracellular magnetic nanoparticle uptake measured by live cell magnetophoresis" extracted from The FASEB Journal Research Communication by Ying Jin, et al.

"Compare Analysis for the Nanotoxicity Effects of Different Amounts of Endocytic Iron Oxide Nanoparticles at Single Cell Level" extracted from PLOS ONE @ www.plosone.org / May 2014 / vol. 9 / issue 5 / e96550 by Chen-Yu Huang et al.

Official Action issued by Taiwan Intellectual Property Office dated Jun. 22, 2017.

* cited by examiner

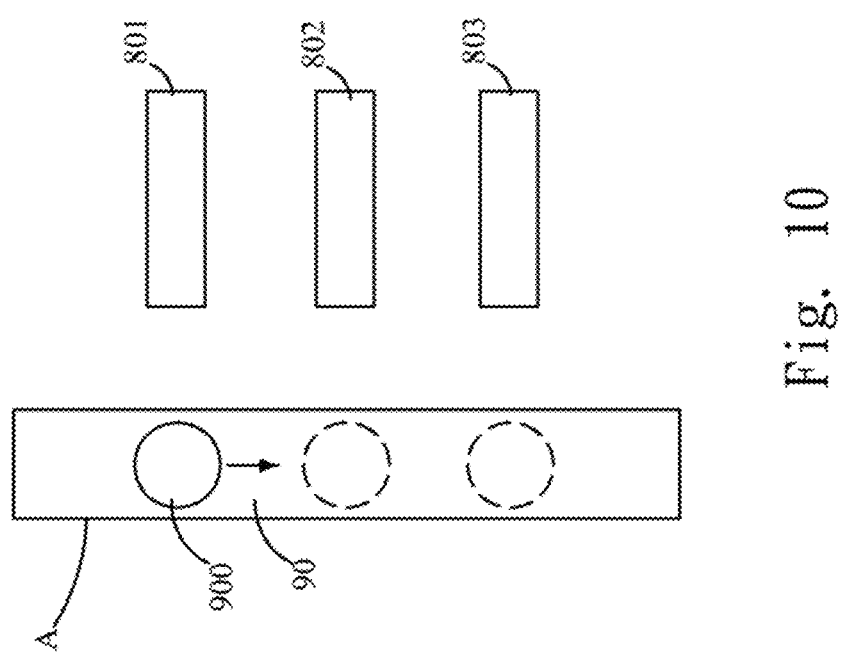

MAGNETOPHORISIS MEASURING SYSTEM FOR DETERMINING MOTION STATUS OF OBJECT AND QUANTIFYING AMOUNT OF MAGNETIC PARTICLES CONTAINED THEREIN

This application claims the benefit of Taiwan Patent Application Serial No. 105137453, filed Nov. 16, 2016, the subject matter of which is incorporated herein by reference.

BACKGROUND OF INVENTION

1. Field of the Invention

The present invention is related to a measuring system, and more particularly, to a magnetophorisis measuring system for determining a motion status of object and quantifying amount of magnetic particles contained therein.

2. Description of the Prior Art

The medical diagnostic instruments are rapidly developed in the recently years, and more particularly, in the diagnostic instrument field, the magnetic nanoparticles are finding increasingly extensive use and are playing a vital role in the biomedical technology. For example, nuclear magnetic resonance (NMR), activation probe, multimodal imaging, drug delivery, and cell labeling, are applied to perform biomedical detection on the cell lines or strains having magnetic nanoparticles stuck on the surfaces thereof or on the organism having magnetic nanoparticles injected therein. However, since the absorption level of magnetic nanoparticles is varied with different kind of cells or strains, how to quantify amount of magnetic nanoparticles being absorbed inside the cell or being stuck on surface of cells becomes an important key in the application fields related to biomedical detection.

Conventionally, a major analysis instrument, called inductively coupled plasma-mass spectrometer (ICP-MS), is utilized to quantify amount of magnetic nanoparticles being engulfed in a cell. Nevertheless, there has some limitations on the ICP-MS. Firstly, the analysis procedures are complicated. Secondly, the cell sample will be damaged during the analysis procedures so that the cell sample cannot be kept intact after the analysis procedures. In addition, the ICP-MS usually has medium-sized or large-sized volume and expensive price so that it can't be popularly used in business and research fields. Alternatively, in US. Pub. No. 20110236882, it disclosed a methods for detecting the presence of nanoparticles or microparticles by cell mass spectrometry (CMS). In this conventional art, CMS is utilized to record a mass spectrum of the cell by cell mass spectrometry in the presence and absence of exposure to the nanoparticle or microparticle, and a shift in mass/charge (m/z) ratio is determined, wherein a shift in the m/z ratio corresponds to an uptake of the nanoparticle or microparticle by the cell. The method further comprises: converting acquired values of m/z and the corresponding charge (z) on each cell to an absolute mass of measured cells.

In addition to the forogingly described mass spectrometry, U.S. Pat. No. 5,974,901 also disclosed a method of quantifying at least one of a plurality of particle physical characteristics. In this conventional art, at first, a region of space having a substantially constant force field is generated. After that, the velocity of at least one particle within the region is determined by identifying and locating the particle and its coordinates in at least two temporally defined digital images, and processing the at least two temporally defined digital images so that the particle is distinct from the background of each temporally defined digital image. Finally, the at least one of a plurality of particle physical characteristics is determined from the determined velocity, and a predetermined force field magnitude and direction.

Moreover, Huang, et al. disclosed "Compare analysis for the nanotoxicity effects of different amounts of endocytic iron oxide nanoparticles at single cell level," *PloS one*, vol. 9, p. e96550, 2014". In this study, Huang disclosed images of moved cells attracted by the magnetic force and moved with constant speed were recorded by a high resolution cooled colored CCD camera, and the displacements of individual cells were tracked via the plug-in "manual tracking" through a link of http://rsb.info.nih.gov/ij/plugins/track/track.html, developed by F. Cordelières. After that, a velocity of moved cells can be calculated thereby obtaining quantities of magnetic nanoparticles contained in each moved particles.

In the conventional magnetophorisis measuring system, when it comes to measure the velocity, the user has to manually mark moved objects so that the system can calculate velocity of the marked objects according to moved distance and required time period. Although the velocity of moved objects can be calculated through manual operation, when there has massive moved objects, it will become more difficult and complicated. Even if the user can measure the velocity one by one, it is time-consuming.

In order to improve the problem caused by the conventional arts, there has a need for providing a magnetophorisis measuring system for determining motion status of object and quantifying amount of magnetic particles contained therein.

SUMMARY OF THE INVENTION

The present invention provides a magnetophorisis measuring system, wherein an external magnetic field is generated to act on a sample liquid such that the objects having magnetic nanoparticles contained therein can generate magnetophorisis phenomenon, and the video with respect to the magnetophorisis phenomenon is captured. After that, an automatic image processing procedure is performed to identify moved object and calculate the magnetophorisis motion status, such as constant velocity motion, constant acceleration motion, or variable acceleration motion, for example. Finally, at least one algorithm is calculated to quantify amount of magnetic nanoparticles according to the measured motion status with respect to the magnetphorisis phenomenon.

The present invention provides a magnetophorisis measuring system for generating an external magnetic field, wherein the gradient direction with respect to the external magnetic field is repeatedly changed so that the objects having magnetic nanoparticles perform a reciprocating magnetophorisis motion in the sample liquid. The amount of objects moved with a specific constant velocity can be quantified and the amount of magnetic nanoparticles corresponding to the specific constant velocity can be calculated in each magnetophorisis motion corresponding to each gradient direction with respect to the external magnetic field. By the reciprocating magnetophorisis motion, a plurality of data sets respectively corresponding to each direction of magnetic field gradient can be obtained thereby reducing inaccuracy of measurement.

The present invention provides a magnetophorisis measuring system, wherein the sample liquid having a plurality of objects is controlled to flow in a one-dimensional flow channel so that the moving direction of each object can be constrained in one-dimensional direction, whereby the quantity of objects moved with a constant velocity can be accurately measured so as to quantify the magnet nanoparticles contained in each object moved with the constant velocity.

In one embodiment, the present invention provides a magnetophorisis measuring system, comprising a microscope, a magnetic field generator, an image acquiring unit, and a processing unit. The microscope is configured to generate a magnified image corresponding to a sample liquid having a plurality of objects, each of which has a plurality of magnetic particles contained therein. The magnetic filed generator is arranged at at least one side of the sample liquid for generating an external magnetic field on the sample liquid whereby the plurality of objects are driven to move. The image acquiring unit is coupled to the microscope for generating a video image with respect to a field of view of the microscope. The processing unit electrically coupled to the image acquiring unit for receiving the video image, wherein the processing unit automatically locks at least one moved object and analyzes a motion status of each moved object, wherein the motion status can be a constant velocity motion, a constant acceleration motion or a variable acceleration motion, and the object can be a bacterial strain, a cell, a protein, an antibody, an antigen, a drug, or a chemical molecular. The magnetophorisis measuring system further comprises a light source module configured to project at least one light beam onto the sample liquid.

In one embodiment, the processing unit divides the video image into a plurality of image frames, finding the at least one moved object according to the at least two image frames, and determines the motion status with respect to each moved object according to a first velocity and a second velocity corresponding to each moved object, wherein the first velocity is determined according to a first time period during which one of the moved objects moved from a first boundary to a second boundary and a distance between the first and second boundaries, and the second velocity is determined according to a second time period during which the one of moved objects moved from the second boundary to a third boundary and a distance between the second and third boundaries.

In one embodiment, the processing unit divides the video image into a plurality of image frames, determines the at least one moved object according to the at least two image frames, and determines the motion status with respect to each moved object according to a first acceleration and a second acceleration corresponding to each moved object, wherein the first acceleration is determined according to a first velocity and a second velocity with respect to the one of moved objects, and the second acceleration is determined according to the second velocity and a third velocity, wherein the first velocity is determined according to a first time period during which one of the moved objects moved from a first boundary to a second boundary and a distance between the first and second boundaries, the second velocity is determined according to a second time period during which the one of moved objects moved from the second boundary to a third boundary and a distance between the second and third boundaries, and the third velocity is determined according to a third time period during which the one of moved objects moved from the third boundary to a fourth boundary and a distance between the third and fourth boundaries.

In one embodiment, the processing unit performs at least one algorithm calculation according to the motion status for quantifying amount of the magnetic particles contained inside each moved object.

In one embodiment, the magnetic field generator changes a magnetic direction of the external magnetic field according to a control signal and the plurality of objects are controlled to perform a reciprocating motion in the sample liquid by repeatedly changing the magnetic direction of the external magnetic field during a measurement of the motion status with respect to the moved objects.

In one embodiment, the magnetic field generator is controlled to change a magnitude of the external magnetic field according to a control signal so as to increase a measurable number of the moved objects and increase a measurable size range of the moved objects.

In one embodiment, the video image comprises a plurality of image frames, and the processing unit performs an image processing procedure and compares a difference between the at least two adjacent image frames for determining the at least one moved object, wherein the processing unit further performs an boundary processing procedure for identifying a boundary contour of each moved object, generates a contour mark corresponding to each moved object, and overlaps the contour mark on the video image.

In one embodiment, the sample liquid is arranged on a one-dimensional horizontal flow channel, a two-dimensional horizontal flow channel, or a vertical flow channel.

In one embodiment, the magnetic field generator can be an electromagnet unit, a permanent magnet unit, or a superconducting magnet unit, wherein the electromagnet unit further comprises a connection bar having two ends, two supporting arms respectively connected to the two ends of the connection bar, and a accommodating space formed between the two supporting arms for accommodating the sample liquid, wherein each supporting arm has a plurality of coils wound thereon.

In one embodiment, the magnetophorisis measuring system further comprises at least one display unit electrically coupled to the image acquiring unit and processing unit for displaying the video image acquired by the image acquiring unit.

All these objects achieved by the magnetophorisis measuring system for determining a motion status of object and quantifying amount of magnetic particles contained therein are described below.

BRIEF DESCRIPTION OF THE DRAWINGS

The present invention will now be specified with reference to its preferred embodiment illustrated in the drawings, in which:

FIG. 10 illustrates one alternative embodiment for determining vertical velocity of moved object.

DESCRIPTION OF THE PREFERRED EMBODIMENT

The invention disclosed herein is directed to a magnetophorisis measuring system for determining a motion status of object and quantifying amount of magnetic particles contained therein. In the following description, numerous details corresponding to the aforesaid drawings are set forth in order to provide a thorough understanding of the present invention so that the present invention can be appreciated by one skilled in the art, wherein like numerals refer to the same or the like parts throughout.

Although the terms first, second, etc. may be used herein to describe various elements, components, modules, and/or zones, these elements, components, modules, and/or zones should not be limited by these terms. Various embodiments will now be described in conjunction with a number of schematic illustrations. The embodiments set forth magnetophorisis measuring system for determining a motion status of object and quantifying amount of magnetic particles contained therein than conventional approaches. Various embodiments of the application may be embodied in many different forms and should not be construed as a limitation to the embodiments set forth herein.

Figure 1:
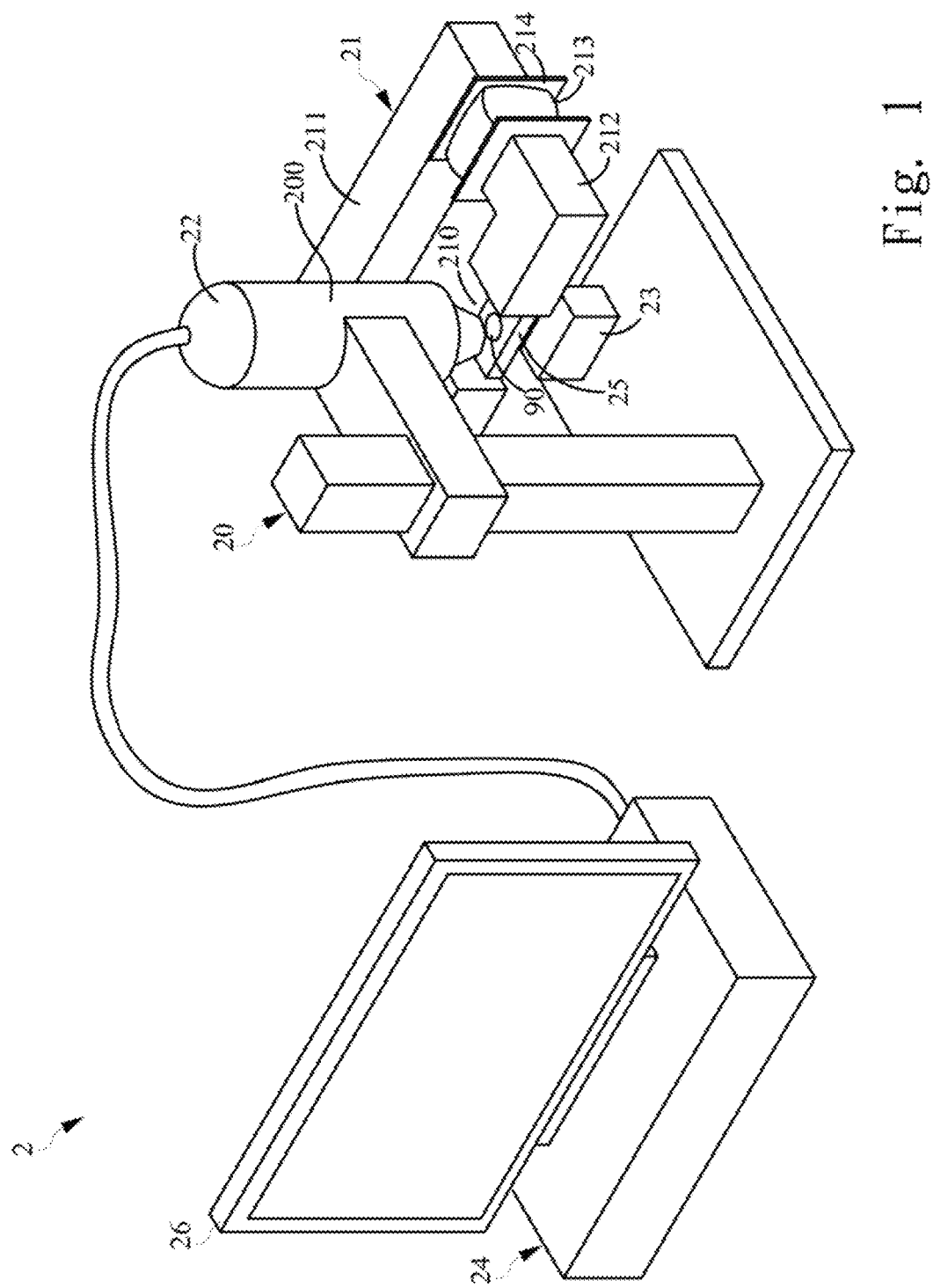
FIG. 1 illustrates a magnetophorisis measuring system according one embodiment of the present invention.

Please refer to FIG. 1, which illustrates a magnetophorsis measuring system according to one embodiment of the present invention. In the present embodiment, the magnetophorisis measuring system 2 comprises a microscope 20, a magnetic field generator 21, an image acquiring unit 22, a light module 23, and a processing unit 24. It is noted that there can be single or several microscopes arranged in the measuring system 2. Each microscope 20 comprises an objective 200 for gathering light from the sample liquid being observed, magnifying the sample liquid, and focusing the light rays to produce a real image. According to the magnification capability selectable for user's requirement, the microscope can be utilized to observe objects having micro or nano scale.

The sample liquid 90 is arranged on a supporting carrier 25. The sample liquid 90 contains a plurality of objects, each of which has a plurality of magnetic particles contained therein. The object can be, but should not be limited to, a bacterial strain, a cell, a protein, an antibody, an antigen, a drug, or a chemical molecular. It is noted that any material that can engulf magnetic particles or has surface to which the magnetic particles can be stuck or attached, can be applied as the object of the present embodiment. In the present embodiment, the plurality of magnetic particles are magnetic nanoparticles and the objects are cells that have capability for engulfing the magnetic particles. It is noted that there has no specific limitation on the quantity of objects and the quantity of the objects is decided according to the user requirement.

In addition, the sample liquid 90 is capable of being arranged in a one-dimensional horizontal micro flow channel, by which the objects in the sample liquid 90 can be constrained to move along one-dimensional direction. Moreover, in one alternative embodiment, the flow channel can also be two-dimensional planar channel such as Petri dish. Alternatively, the flow channel can be a one-dimensional micro flow channel arranged vertically. The type of flow channel for accommodating the sample liquid 90 is determined according to the user requirement.

Figure 2:
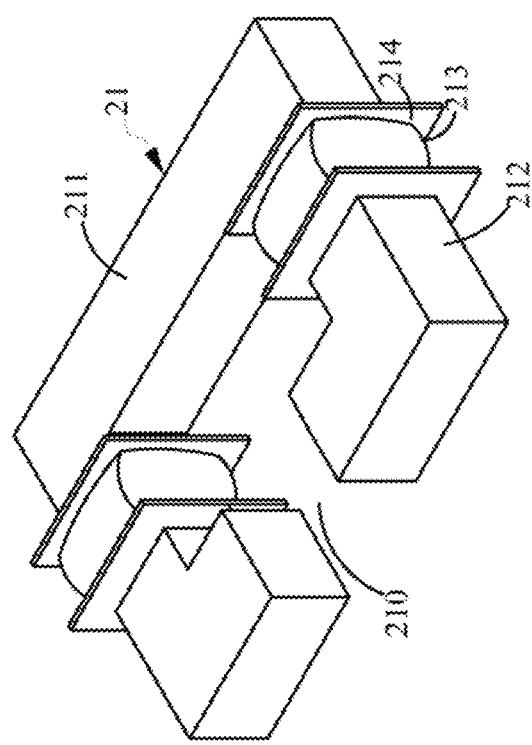
FIG. 2 illustrates a perspective view of a magnet field generator according to one embodiment of the present invention.

The magnetic field generator 21 is arranged at one side or two sides of the sample liquid 90 for generating an external magnetic field on the sample liquid whereby the objects inside the sample liquid 90 can be driven to move. It is noted that there can be single magnetic field generator or several magnetic field generators arranged at least one side of the sample liquid 90. In the present embodiment, as shown in FIG. 2, the magnetic field generator 21 is an electromagnet having coils electrically coupled to an electrical power. The magnetic field generator 21 has an accommodating space 210 for accommodating the sample liquid 90. The magnetic field generator 21 is actuated to generate the external magnetic field by receiving the electrical energy. In the present embodiment, the magnetic field generator 21 comprises a connection bar 211 having two ends, two supporting arms 212 with a plurality of coils wound thereon respectively connected to the two ends of the connection bar 211, and the accommodating space formed between the two supporting arms 212 for accommodating the sample liquid.

It is noted that the shape of the arm 212 is determined according to user's need and is not limited to the shape shown in FIG. 2. In the present embodiment, the arm 212 is L-shaped arm, but should not be construed as being limited thereto. Each L-shaped arm has coils 213 wound around thereon. In order to enhance the wound effect of coils 213 around the arm 212, block plates 214 can be arranged at the two sides of coils 213 wound around each arm 212. In addition to electromagnet, the magnetic field generator 21 can also be a permanent magnet unit or superconducting unit. Please referring back to FIG. 1, when the magnetic field generator 21 receives electrical energy, the external magnetic field can be generated to act on the sample liquid 90. Since the magnetic particles inside each object are affected by the external magnetic field, the objects can be driven to move along the direction of the external magnetic field. In one embodiment, the magnetic field generator 21 is electrically coupled to the processing unit 24. The processing unit 24 can control the ON/OFF of electric energy through a control signal thereby controlling the ON/OFF of the external magnetic field acting on the sample liquid.

The light module 23 is configured to generate a light field projecting onto the sample liquid 90 so that the sample liquid 90 can be observed by the microscope 20. It is also noted that there can be single or several light modules arranged at a side of the sample liquid 90. In the present embodiment, the light module 23 is arranged under the sample liquid 90. There has no specific limitation on the color of light field generated by the light module 23. The light field can be a white light field or specific color light field. In another embodiment, in case of the object that can be excited to generate fluorescent light, the light module 23 can be a module, such as laser module, that can generate light for exciting the objects to generate fluorescent light.

The image acquiring unit 22 is coupled to the microscope 20 for acquiring a video image with respect to the sample fluid 90 within the view field of the microscope, wherein the video image records motion status of each moved objects in the sample liquid. The video image generated by the image acquiring unit 22 is further transmitted to the processing unit 24. It is noted the number of the image acquiring unit 22 is corresponding to the number of the microscopes. In one embodiment, the system 2 further comprises a display unit 26 for simultaneously displaying the video image acquired by the image acquiring unit 22. In another alternative embodiment, the microscope 20, magnetic field generator 21, image acquiring unit 22, light module 23, and processing unit 24 are integrated into a housing so as to make the system 2 become a portable and compact magnetophorisis measuring system.

When the processing unit 24 receives the video image, the processing unit 24 can perform a processing procedure for locking each moved objects automatically and analyzing the motion status corresponding each moved object, wherein the motion status can be, but should not be limited to, a constant velocity motion, a constant acceleration motion or a variable acceleration motion. Taking constant velocity motion as an example, since the liquid sample 90 possesses a viscosity, the viscosity force acting on each object can be represented by $F_{vis}$ and is expressed as equation (1) listed below:

$$F_{vis}=6\pi\eta Rv \quad (1),$$

wherein v represents velocity, R represents radius of each object (cell), η represents viscosity of sample liquid. When the external magnetic field acts on the objects in the sample liquid, the objects will be driven to move, wherein the magnetic force acting on the objects can be expressed as equation (2) listed below:

$$FB=m_{bead}dB/dx \quad (2),$$

wherein dB/dx represents gradient of magnetic field, $m_{bead}$ is a constant which is equal to $NbMs\pi D^3/6$, wherein N represents the quantities of magnetic particles, b represents a ratio of magnetic field and magnetic susceptibility, Ms represents magnetic susceptibility, and D represents diameter of magnetic particle.

According to the abovementioned equation (1) and (2), when the viscosity force is equal to the magnetic force, the resultant force acting on the object is equal to zero whereby the object can perform a constant velocity motion. Therefore the equation (1) is equal to equation (2) so that the quantities of magnetic particles N in each object having constant velocity motion can be expressed by the equation (3) listed below:

$$N = \frac{36\eta R_{cell} V}{bM_s d^3 dB/dx} \quad (3)$$

The abovementioned embodiment shows that the number of magnetic particles in the moved objects is calculated according to equation (3) when the objects moved once time from one side to the other side within the view field of the microscope. However, in some occasions that may be causes affected the accuracy of calculation, for example, when the objects move closing to the boundary of flow channel or closing to the magnetic field generator, the accuracy of quantifying the magnetic particles may be affected. Therefore, in another alternative embodiment, the processing unit 24 can generate a control signal for controlling the magnetic field generator to change the direction of the external magnetic field. For example, in a first time period, the external magnetic field having a first magnetic direction is acting on the sample liquid 90 whereas, in a second time period, the processing unit 24 controls the magnetic field generator to generate external magnetic field having a second magnetic direction acting on the sample liquid 90. The control of the magnetic direction can be operated repeatedly through a plurality of times so that the objects within the sample liquid can perform a reciprocating motion under the external magnetic field. In the reciprocating motion of the objects, the magnetic particles can be quantified according to the equation (3) when the objects moved from a first side to a second side as well as when the objects moved from the second side to the first side. During the time period where the objects perform the reciprocating motion, a plurality of velocity data respectively corresponding to each time of motion can be obtained to calculate the number of magnetic particles in each object. After a statistic calculation, the inaccuracy consequence induced by the abovementioned causes can be eliminated so as to enhance the accuracy of measurement.

In addition, in another embodiment, in order to overcome the issue that the magnitude of external magnetic field causing the object to perform magnetophorisis motion will be varied with the size of the objects, or issue that the magnetic particles engulfed by the object is insufficient, the magnetic field generator can be controlled to change the magnitude of the external magnetic field through a control from the processing unit 24, whereby the objects having different size from each other or having insufficient magnetic particles can also generate magnetophorisis motion so that a measurable number of the moved objects can be increased and a measurable size range of the moved objects can be expanded.

Next, a method that how the processing unit 24 identifies the moved objects and determines the motion status of each moved object is explained in detail in the following embodiments. In the one embodiment, the processing unit 24 having processing and calculating capability can be, but should not be limited to, a computer, notebook, workstation or motherboard with central processing unit (CPU) for executing at least one program with respect to the flows shown in FIGS. 3 and 4.

Figure 7:
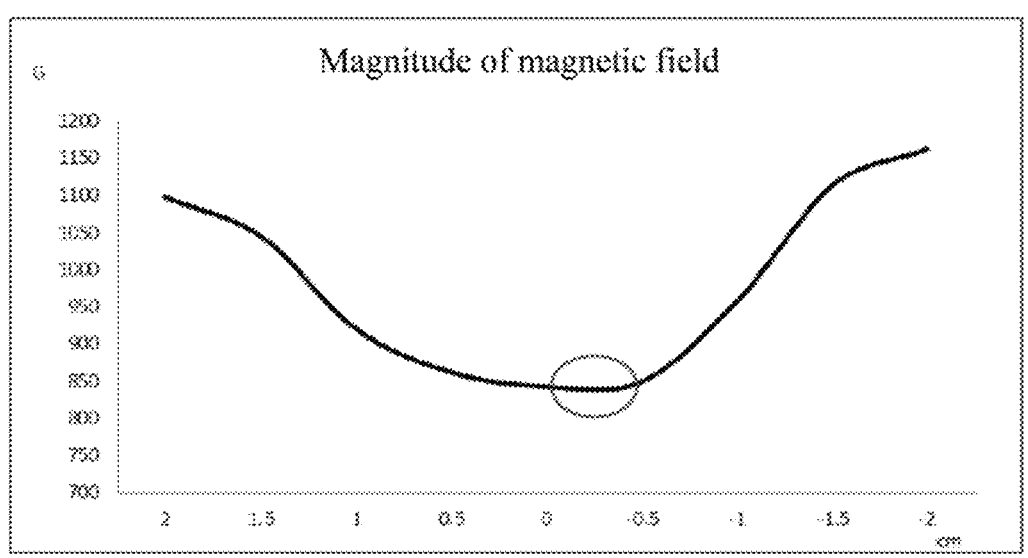
FIG. 7 shows a relation between magnetic field magnitude and distance.

At first, the gradient distribution about the magnetic field is explained. Please referring to FIG. 7, the gradient of magnetic field is varied with the position within the area exerted by the external magnetic field. For example, in the embodiment shown in FIG. 7, the electric current is fixed at 0.84 A, and the curve illustrates a variation with respect to position measured every 0.5 cm along the magnetic gradient direction. According to the curve shown in FIG. 7, the two opposite end areas around the two supporting arms have largest magnitude of magnetic field, respectively, whereas, in the central area such as the elliptical area shown in FIG. 7, the variation of gradient of magnetic field is slowed down. Accordingly, the area with gentle variation of gradient of magnetic field, such as the elliptical area shown in FIG. 7, is suitable to be an observation area of magnetophorisis motion. In one embodiment, the magnification of microscope is adjusted to be 20× for observing the magnetophorsis motion in the observation area. Through the boundary definition in the observation area, the motion of each moved object can be determined.

Figure 3:
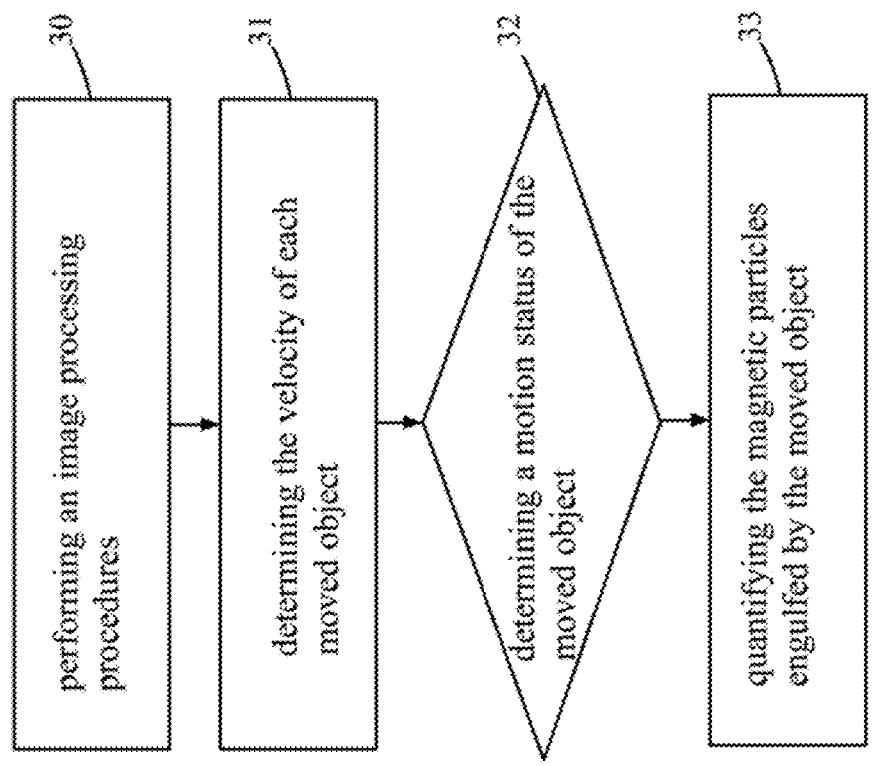
FIG. 3 illustrates a flow chart for determining if the object performs a constant motion and quantifying magnetic nanoparticles according to one embodiment of the present invention.
Figure 4:
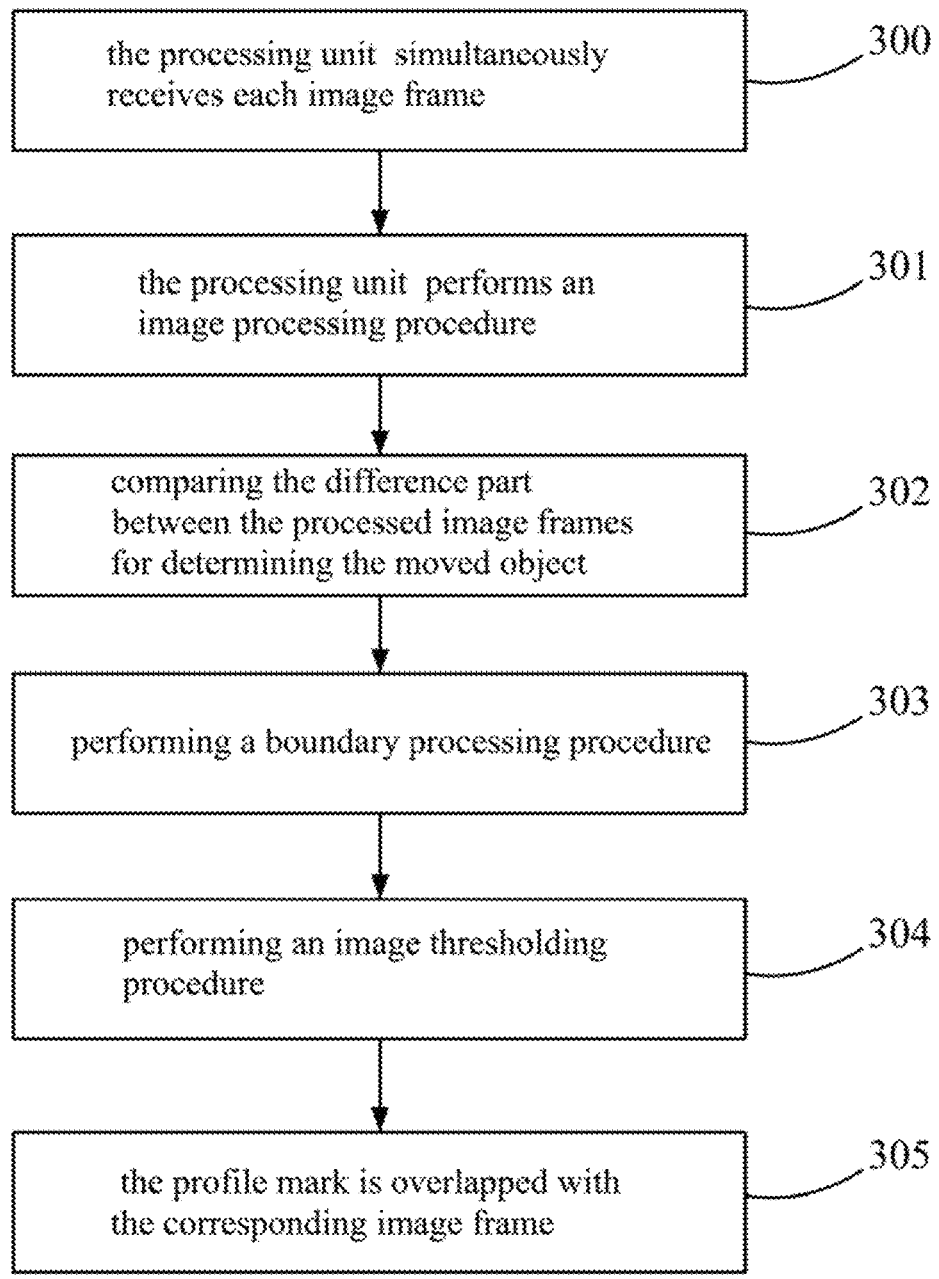
FIG. 4 is a flow chart illustrates procedures for processing the video image acquired by the image acquiring unit according to one embodiment of the present invention.
Figure 5A:
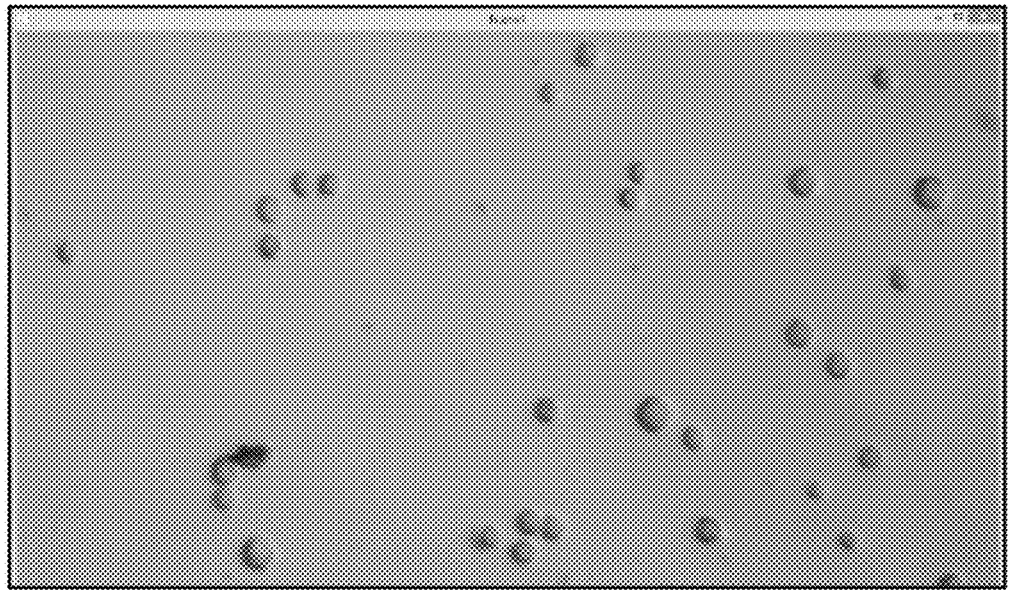
FIGS. 5A-5E illustrates image processing result according to the procedures shown in FIG. 4.

The video image captured by the image acquiring unit 22 comprises a plurality of sequential image frames, each of which is transmitted to the processing unit 24 and is processed according to the steps shown in FIG. 3. In the step 30, the processing unit 24 performs an image processing procedures shown in FIG. 4. The steps shown in FIG. 4 are explained below. In step 300, the processing unit 24 simultaneously receives each image frame, such as the image shown in FIG. 5A, acquired by the image acquiring unit 22. Next, in the step 301, the processing unit 24 performs an image processing procedure, including algorithm of conversion and/or calculation. In one embodiment, it can be, but should not be limited to, a gray scale conversion. In the present step, since each image frame is converted into a gray scale image, some noise color can be eliminated thereby improving the result of identifying background and moved object, and reducing the amount of data processing so that the processing and calculation efficiency can be enhanced.

Figure 5B:
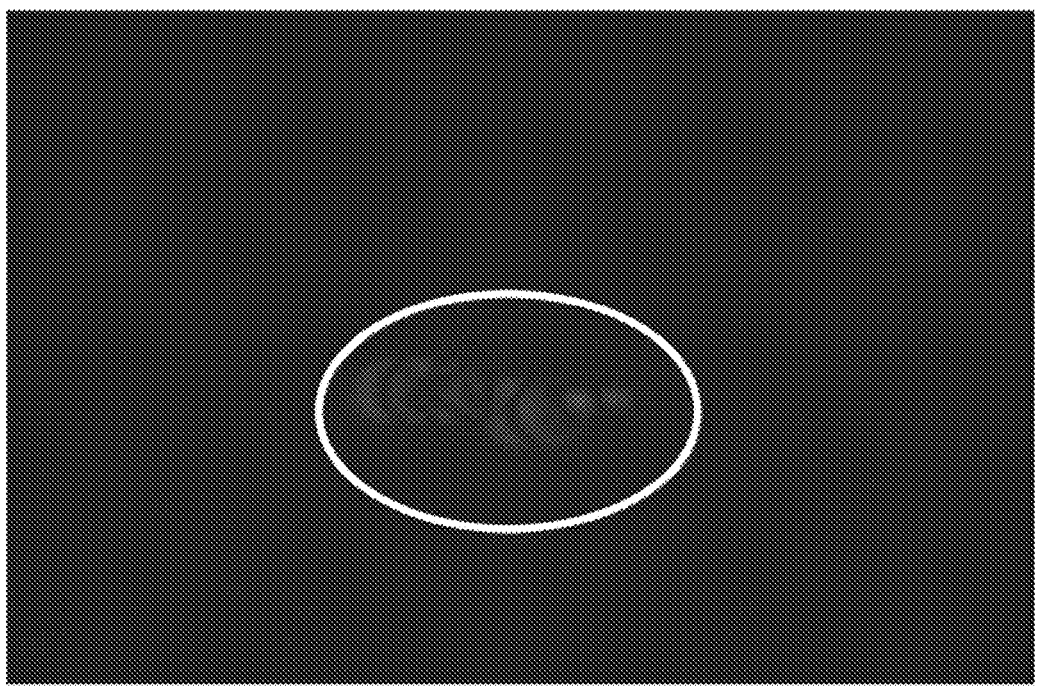

After the step 301, the step 302 is performed to compare the difference part between the processed image frames for determining the moved object. In one embodiment, FIG. 5B illustrates a comparing result of step 302 wherein the elliptical area represents intensity of moved objects in the plurality of processed image frames. Once the moved objected is identified, a step 303 shown in FIG. 4 is executed to perform a boundary processing procedure. In one embodiment, the boundary processing procedure includes, but should not be limited to, a edge enhancement, sharpness enhancement, blur process for reducing affection of noises, or combination thereof.

Figure 5C:
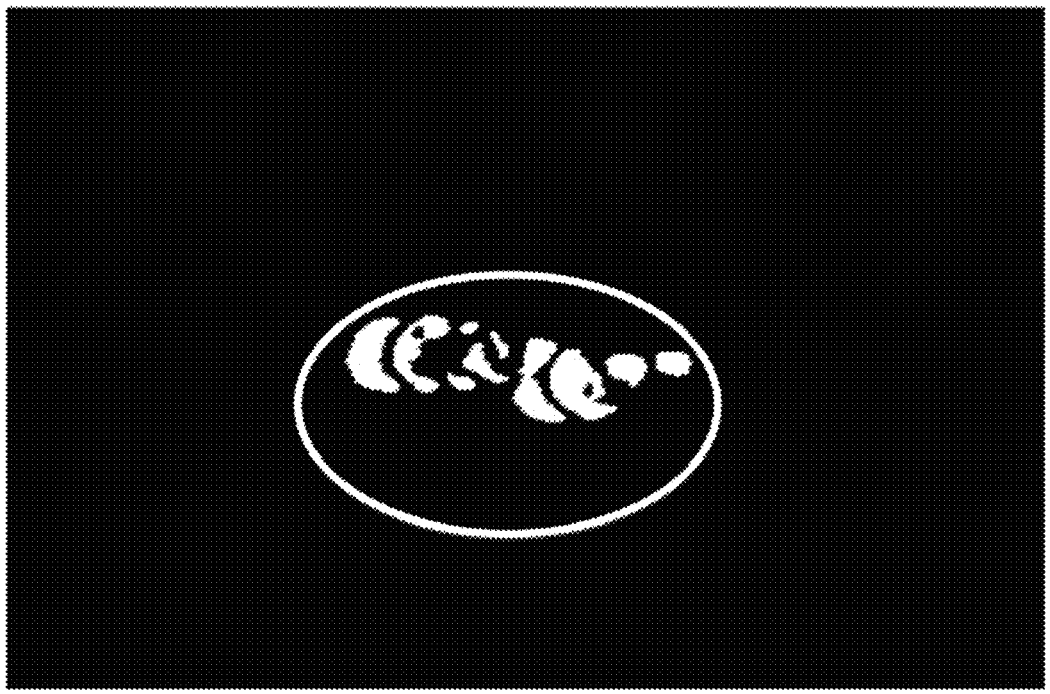
Figure 5D:
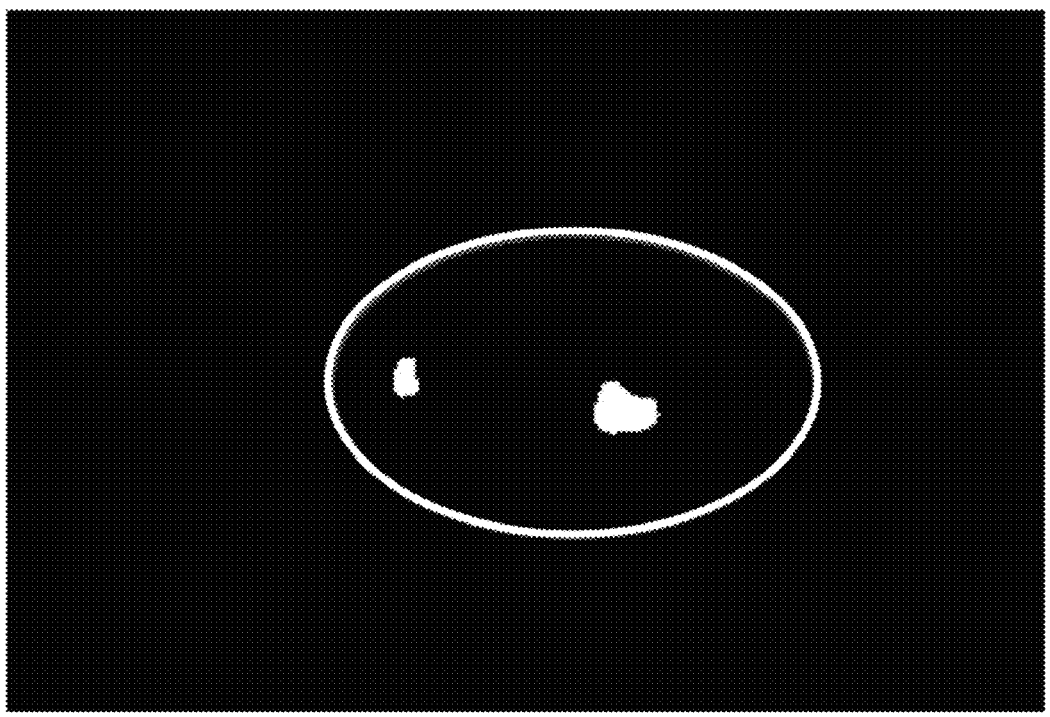
Figure 5E:
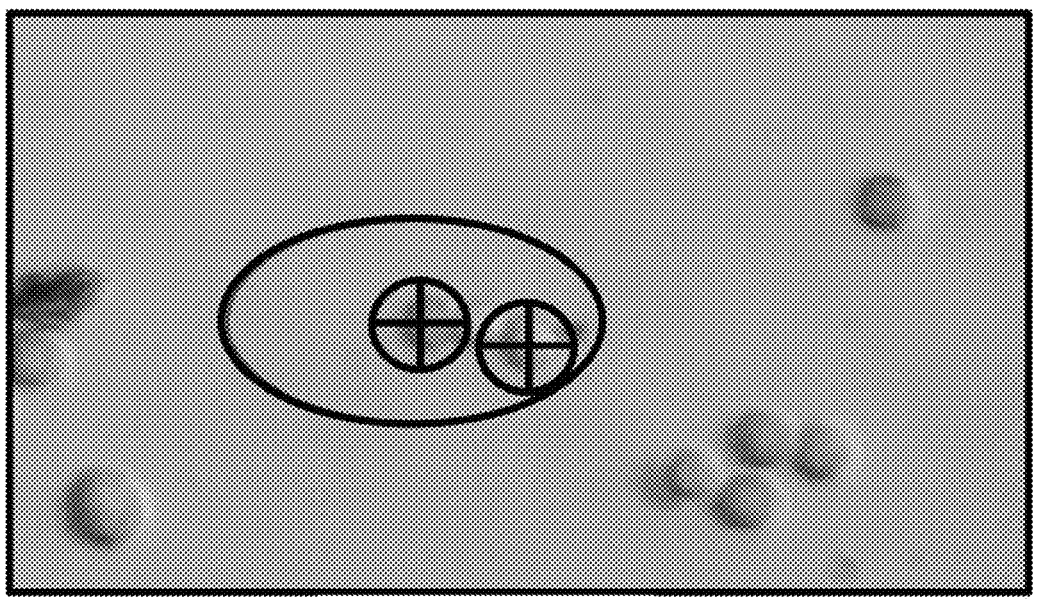

Through the boundary processing procedure, the profile of the moved object can be easily identified. Please refer to FIG. 5C, which illustrates a consequence of boundary processing procedure according to one embodiment of the present invention. Finally, a step 304 is executed to perform an image thresholding procedure so that the image generated by step 303 can be converted into a binary image, i.e. only black or white in each pixel of the binary image. FIG. 5D illustrates one embodiment of step 304, wherein the white area represents the moved object. In order to assist the user to identify the moved object, in one embodiment, an image of profile mark with a specific color is further generated through step 305 and the profile mark is overlapped with the corresponding image frame. The consequence of step 305 is output to the display unit 26 so that the display unit can display the video image having profile mark onto the moved object. FIG. 5E illustrates one embodiment of the consequence of step 305. When the steps 300~305 are repeatedly executed, the moved objects in the sample liquid can be traced and shown on the display unit 26 whereby the user can easily observe the moved object.

Figure 6A:
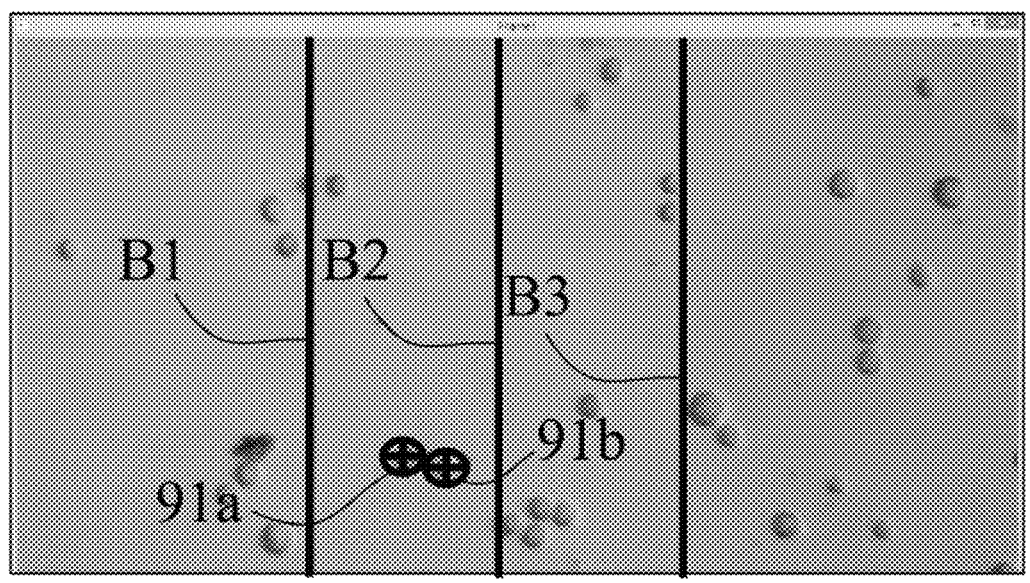
FIGS. 6A and 6B illustrates one embodiment for calculating velocity of moved objects.

Returning to FIG. 3, after the step 30 for identifying the moved object, step 31 is utilized to determine the velocity of each moved object. In one embodiment, since the view field of microscope has fixed size, three virtual boundary lines B1~B3 can be defined, wherein the distances between two boundary lines are know. As shown in FIG. 6A, the distance between two boundary lines can be the same as each other. Alternatively, the distance can be different from each other. When the moved object passes boundary line B1, the processing unit 24 starts counting the time. In one embodiment, the time counting is determined according to the frame rate. After the moved object passes the second boundary line B2, the processing unit 24 can calculate velocity of the moved object 91a and 91b according to equation (4) listed below, wherein D represents distance between B1 and B2, T represents time, (X1, Y1) represents a position on boundary line B1, and (X2, Y2) represents a position on boundary line B2. Likewise, after the moved object passes the second boundary line B2, the processing unit 24 starts counting the time required between boundary B2 and B3, and the move objects continue to move toward boundary line B3. In the equation (4) the time is determined according to the multiplying result of frame number with respect to one moved object from the one boundary line to the next boundary line, e.g. boundary line B1 and boundary line B2, and frame rate of the image acquiring unit. After the moved object passes the second boundary line B3, the processing unit 24 can calculate velocity of the moved object 91a and 91b according to equation (4). Once the velocity of the moved objects with respect to the area between boundary lines B1 and B2, and B2 and B3 is respectively obtained, the step 32 is performed to determine a motion status of the moved object according to the velocity obtained in step 31. In one embodiment, when the velocity between boundary lines B1 and B2 and velocity between boundary lines B2 and B3 are equal to each other, the motion status of the moved objects is determined as a constant velocity motion.

$$v(\mu m/s) = \frac{D}{T} = \frac{\sqrt{(X_2 - X_1)^2 + (Y_2 - Y_1)^2} \, (\mu m)}{\text{frame numbers} \times (1/FrameRate)(s)} \quad (4)$$

Figure 6B:
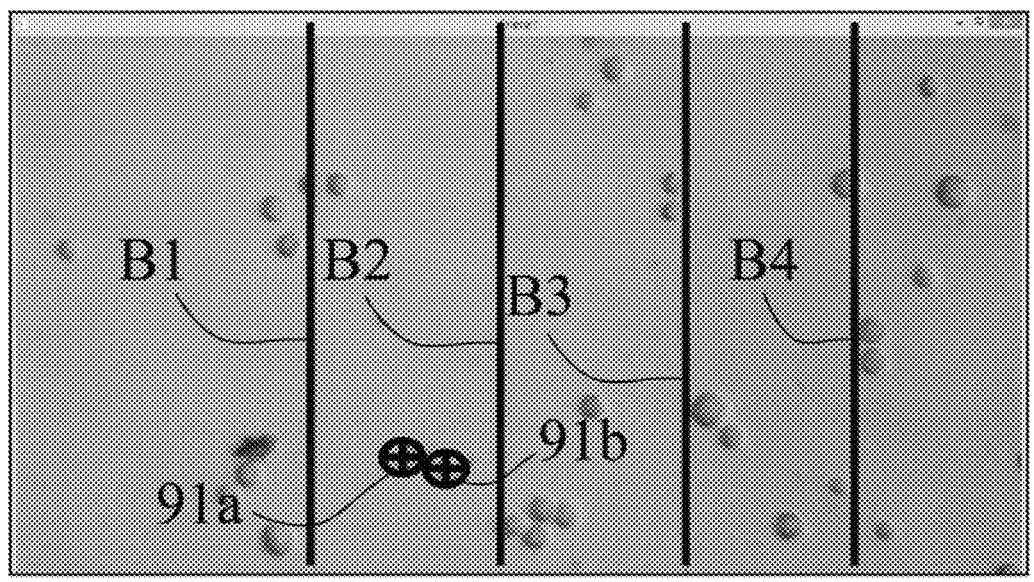

In addition, in another embodiment, the motion status can be constant acceleration motion or variable acceleration motion. When it comes to determine if the moved object is under constant acceleration motion or variable acceleration motion, the number of boundary lines in step 31 is varied but is operated according to the same principle as the step 31. Please referring to FIG. 6B, in step 31, four boundary lines B1~B4 is utilized. According to the foregoingly described method, the boundary lines B1 and B2 can be utilized to determine a first velocity V1, and the boundary lines B2 and B3 can be utilized to determine a second velocity V2. Likewise, the boundary lines B3 and B4 can be utilized to determine a third velocity V3. Since the time between V1 and V2 is known, so a first acceleration can be determined according to first and second velocities V1 and V2. Likewise, the time between V2 and V3 is known, so a second acceleration can be determined according to first and second velocities V2 and V3.

Once the first and second accelerations are determined the motion status of moved objects such as constant acceleration motion or variable acceleration motion can be determined. It is noted that although the equation (3) is an equation for quantifying the magnetic particles within the moved object under constant velocity motion, the parameter V in the equation (3) can be adjusted properly for constant acceleration or variable acceleration thereby quantifying the magnetic particles when the moved object is moved under constant acceleration or variable acceleration.

Please referring back to FIG. 3, once the moved object is not moved with a constant velocity, the processing unit 24 will return the first step 30 to find another moved object and repeat the steps 30~32; however, if the moved object is moved with a constant velocity, step 33 will be performed by using the equation (3) to quantify the magnetic particles engulfed by the moved object. The steps 30~33 can immediately detect and measure the velocity several moved objects without destroying the structure of each moved objects so that the objects in the sample liquid can be reused.

Figure 8:
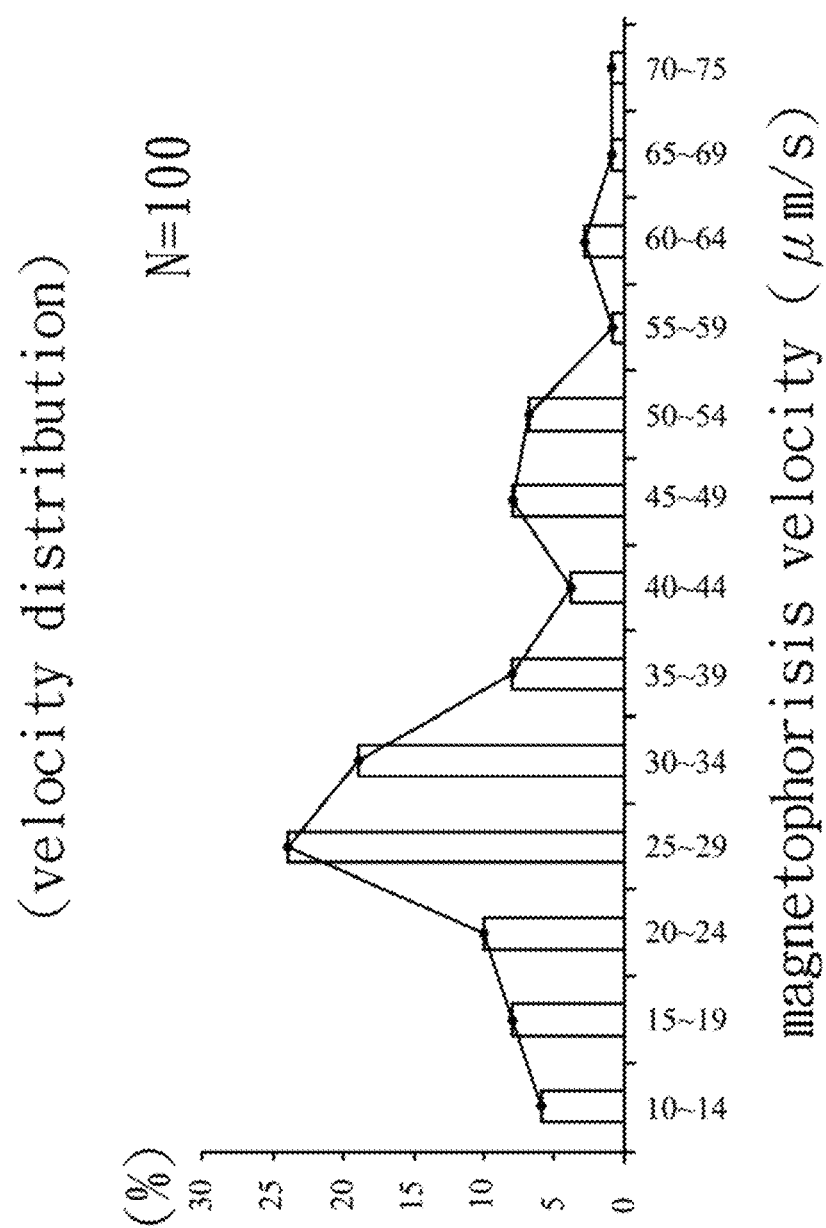
FIG. 8 illustrates a velocity distribution of the moved objects under a specific magnitude of magnetic field.

According to the experimental result in one embodiment illustrated in FIG. 8, for example, under a magnetic field strength of 843 Gauss, the velocity distribution of magnetophorisis motion per 100 objects is from 25-29 μm/s, and the average velocity is 33 μm/s. According to the equation (3), the average amount of the magnetic particles in each moved object is 28,825. Since the total number of objects is known, and volume and density of magnetic particle is known as well, the iron content contained in each object can be calculated to be 0.68 ppm (μg), which is close to the result 0.659 ppm (μg) obtained by ICP-MS. According to the previous measuring result, since the embodiment of the present measuring system that is low establishing cost and will not destroy the objects during the measuring procedure can obtain the similar result with that obtained by ICP-MS which has higher establishing cost and will destroy the objects during the measuring procedure, the system of the present invention can be easily and potentially popularized in various kinds of application field.

Figure 9:
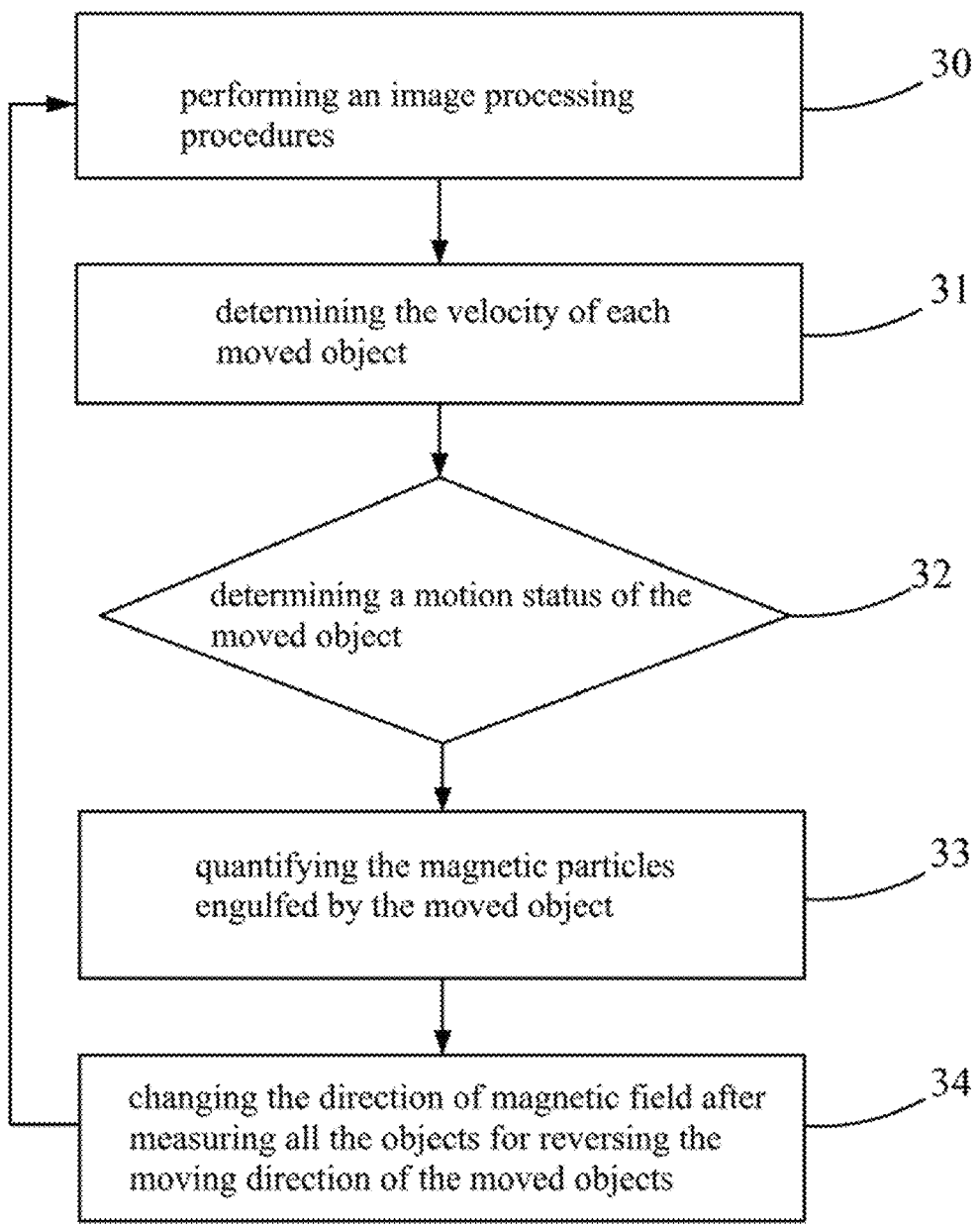
FIG. 9 illustrates a flow chart for determining if the object performs a constant motion and quantifying magnetic nanoparticles according to another embodiment of the present invention.

Please refer to FIG. 9, which illustrates another embodiment of flow for quantifying the magnetic particles of moved object. The flow chart of the present embodiment is basically the same as the flow chart shown in FIG. 3. The different part is that a step 34 is performed to reduce the inaccuracy or error of quantifying the magnetic particles in each object. In step 34, the processing unit 24 further controls the magnetic field generator 21 to change the direction of magnetic field after measuring all the objects whereby the objects reverse the moving direction. During the motion in reversing direction, the steps 30~33 are executed again thereby obtaining velocity distribution. By means of a plurality of times reciprocating motion through change of magnetic direction, the inaccuracy or error can be reduced by a statistic calculation on the measured data.

In addition, it is noted when the flow channel in the abovementioned embodiment is the one-dimensional flow channel, the flow direction of each moved object is constrained in a single direction. However, in alternative embodiment, when there has a depth in the flow channel such as Petri dish, or vertical flow channel, the velocity of the moved object can be calculated if the focus/defocus effect is under recognizable range when steps 30~33 are performed. In this condition, the velocity of moved objects under different depth in the flow channel can also be calculated immediately so as to improve the measuring efficiency. Alternatively, when vertical channel designed to allow single object to move is adapted, the size of focus/defocus object can also be utilized to determine the depth position of the moved object thereby determining the velocity of the moved object along the depth direction. Regarding to the relationship between the focus/defocus size and depth, a database can be established in advance so that when the size of the moved object is determined, the depth can be determined according to the data established in the database.

Alternatively, in another embodiment where the object moved along a vertical direction, the light module 23 can also assist to detect the velocity of moved object along the depth direction or vertical direction. In this embodiment, the light module 23 further comprises a plurality of laser light sources respectively arranged at different depth. The distance between two adjacent laser light sources is known. It is noted that the position of the laser light source is corresponding to the boundary lines shown in FIG. 6A or FIG. 6B. For example, in one embodiment, the flow channel diameter is controlled to allow a single object flowing therethrough. When the moved object passes the position corresponding to the laser light source, the receiver opposite the laser light source will not receive the laser light and the processing unit can record the first timing. Likewise, when the moved object passes another position corresponding to the other laser source, the second timing is recorded. In one embodiment, the timing can be determined according to the frame rate. Alternatively, an image processing procedure can be utilized by the processing unit, in which a time difference between a first time point that the moved object is projected by one of the two adjacent laser light source and a second time point that the moved object is projected by the other one of the two adjacent laser light sources can be know through the image processing procedure. For example, in FIG. 10, the image acquiring unit recording a continuous image when the moved object 900 of the sample liquid 90 in the channel A moved from one laser light source 801 to the next adjacent laser light source 802. Since the laser light sources 801~803 arranged along the vertical direction are active to project laser light toward the channel A, the moved object 900 will be projected to become clearly visible in the continuous image and can be identified through the image processing procedure operated by the processing unit such that the time difference between a first time point that the moved object 900 is projected by the laser light source 801 and second time point that the moved object is projected by the laser light source 802 can be known. Since the distance between two adjacent laser light sources is known and the time difference is known, the velocity of the moved object can be determined. Accordingly, three laser light sources can be utilized to determine if the moved object is moved under constant velocity motion or not, while four laser light sources can be utilized to determine if the moved object is moved under constant acceleration motion or variable acceleration motion. Alternatively, an image processing method can also be utilized to identify if the moved object is projected by the laser light or not, and the identification result can also be utilized to determine the motion status of each moved object.

According to the abovementioned embodiments, the present invention provides a magnetophorisis measuring system, wherein the external magnetic field acts on the sample liquid containing objects having magnetic nanoparticles so that the objects generate magnetophorisis phenomenon and an automatic image processing procedure is performed to determine the motion status of moved object so that the magnetic particles in each moved object can be quantified. Through the measuring system of the present invention, the objects will not be destroyed and the objects in the sample liquid can be reused after the measuring procedure; therefore, the sample resource, especially the precious sample, can be saved, and the measuring efficiency can be greatly improved because the steps of manual procedure for marking the moved object is not necessary. Furthermore, a plurality of measuring data can be obtained through a direction control of magnetic field so that the inaccuracy or error of measuring result can be reduced.

While the present invention has been particularly shown and described with reference to a preferred embodiment, it will be understood by those skilled in the art that various changes in form and detail may be without departing from the spirit and scope of the present invention.

What is claimed is:
1. A magnetophorisis measuring system, comprising:
at least one microscope, configured to generate a magnified image corresponding to a sample liquid having a plurality of objects, each of which has a plurality of magnetic particles contained therein;
at least one magnetic filed generator, arranged at at least one side of the sample liquid for generating an external magnetic field acting on the sample liquid whereby the plurality of objects are driven to move, wherein the magnetic field generator changes a magnetic direction of the external magnetic field according to a control signal and the plurality of objects are controlled to perform a reciprocating motion in the sample liquid by repeatedly changing the magnetic direction of the external magnetic field during a measurement of the motion status with respect to the moved objects;

at least one image acquiring unit, respectively coupled to the at least one microscope for receiving the magnified image thereby generating a video image with respect to a field of view of the microscope; and at least one processing unit, electrically coupled to the at least one image acquiring unit for receiving the video image, wherein the processing unit automatically locks at least one moved object and analyzes a motion status of each moved object;

wherein the processing unit divides the video image into a plurality of image frames, identifies the at least one moved object according to the at least two image frames, and determines the motion status with respect to each moved object according to a first velocity and a second velocity corresponding to each moved object, wherein the first velocity is determined according to a first time period during which one of the moved objects moved from a first boundary line to a second boundary line, and a distance between the first and second boundary lines, and the second velocity is determined according to a second time period during which the one of moved objects moved from the second boundary line to a third boundary line, and a distance between the second and third boundary lines, wherein the first time period is determined according to a frame number related to one of the moved objects moved from the first boundary line to the second boundary line and a frame rate of the image acquiring unit, and the second time period is determined according to a frame number related to the one of the moved objects moved from the second boundary line to the third boundary line and the frame rate of the image acquiring unit.

2. The system of claim 1, wherein the motion status is a constant velocity motion, a constant acceleration motion or a variable acceleration motion.

3. The system of claim 1, wherein the processing unit performs at least one algorithm calculation according to the motion status for quantifying amount of the magnetic particles contained inside each moved object.

4. The system of claim 1, wherein the magnetic field generator is controlled to change a magnitude of the external magnetic field according to a control signal so as to increase a measurable number of the moved objects and increase a measurable size range of the moved objects.

5. The system of claim 1, wherein the sample liquid is arranged on a one-dimensional horizontal flow channel, a two-dimensional horizontal flow channel, or a vertical flow channel.

6. The system of claim 1, wherein the object is a bacterial strain, a cell, a protein, an antibody, an antigen, a drug, or a chemical molecular.

7. The system of claim 1, further comprising at least one display unit electrically coupled to the image acquiring unit and the processing unit for displaying the video image acquired by the image acquiring unit.

8. The system of claim 1, wherein the magnetic field generator is an electromagnet unit, a permanent magnet unit, or a superconducting magnet unit.

9. The system of claim 8, wherein the electromagnet unit further comprises a connection bar having two ends, two supporting arms respectively connected to the two ends of the connection bar, and a accommodating space formed between the two supporting arms for accommodating the sample liquid, wherein each supporting arm has a plurality of coils wound thereon.

10. The system of claim 1, wherein the video image comprises a plurality of image frames, and the processing unit performs an image processing procedure and compares a difference between the at least two adjacent image frames for identifying the at least one moved object.

11. The system of claim 10, wherein the image processing procedure comprises a gray scale conversion for eliminating a noise color thereby improving result of identifying background and the at least one moved object, and reducing data processing amount.

12. The system of claim 10, wherein the processing unit further performs a boundary processing procedure for identifying a boundary contour of each moved object, generates a contour mark corresponding to each moved object, and overlaps the contour mark on the video image.

13. The system of claim 1, further comprising a light source module configured to project at least one light beam onto the sample liquid.

14. The system of claim 13, wherein the moved object further moved along a vertical direction, the light source module further comprises a plurality of laser light sources respectively arranged at different depths along the vertical direction.

15. The system of claim 14, wherein a velocity with respect to the moved object can be determined according to a known distance between two adjacent laser light sources, and a time difference between a first time point that the moved object is projected by one of the two adjacent laser light sources and a second time point that the moved object is projected by the other one of the two adjacent laser light sources.

16. A magnetophorisis measuring system, comprising:

at least one microscope, configured to generate a magnified image corresponding to a sample liquid having a plurality of objects, each of which has a plurality of magnetic particles contained therein;

at least one magnetic filed generator, arranged at at least one side of the sample liquid for generating an external magnetic field acting on the sample liquid whereby the plurality of objects are driven to move, wherein the magnetic field generator changes a magnetic direction of the external magnetic field according to a control signal and the plurality of objects are controlled to perform a reciprocating motion in the sample liquid by repeatedly changing the magnetic direction of the external magnetic field during a measurement of the motion status with respect to the moved objects;

at least one image acquiring unit, respectively coupled to the at least one microscope for receiving the magnified image thereby generating a video image with respect to a field of view of the microscope; and at least one processing unit, electrically coupled to the at least one image acquiring unit for receiving the video image, wherein the processing unit automatically locks at least one moved object and analyzes a motion status of each moved object;

wherein the processing unit divides the video image into a plurality of image frames, identifies the at least one moved object according to the at least two image frames, and determines the motion status with respect to each moved object according to a first acceleration and a second acceleration corresponding to each moved object, wherein the first acceleration is determined according to a first velocity and a second velocity with respect to the one of moved objects, and the second acceleration is determined according to the second velocity and a third velocity, wherein the first velocity is determined according to a first time period during which one of the moved objects moved from a first boundary line to a second boundary line and a distance between the first and second boundary lines, the second velocity is determined according to a second time period during which the one of moved objects moved from the second boundary line to a third boundary line and a distance between the second and third boundary lines, and the third velocity is determined according to a third time period during which the one of moved objects moved from the third boundary line to a fourth boundary line and a distance between the third and fourth boundary lines, wherein the first time period is determined according to a frame number related to the one of the moved objects moved from the first boundary line to the second boundary line and a frame rate of the image acquiring unit, the second time period is determined according to a frame number related to the one of the moved objects moved from the second boundary line to the third boundary line and the frame rate of the image acquiring unit, and the third time period is determined according to a frame number related to the one of the moved objects moved from the third boundary line to the boundary line and the frame rate of the image acquiring unit.

* * * * *